US012390720B1

(12) United States Patent
Peterson

(10) Patent No.: US 12,390,720 B1
(45) Date of Patent: Aug. 19, 2025

(54) AROMA CARTRIDGE FOR A GAMING SYSTEM

(71) Applicant: Richard B. Peterson, Haslet, TX (US)

(72) Inventor: Richard B. Peterson, Haslet, TX (US)

( * ) Notice: Subject to any disclaimer, the term of this patent is extended or adjusted under 35 U.S.C. 154(b) by 261 days.

(21) Appl. No.: 18/233,306

(22) Filed: Aug. 12, 2023

(51) Int. Cl.
*A63F 13/28* (2014.01)
*A61L 9/14* (2006.01)

(52) U.S. Cl.
CPC .............. *A63F 13/28* (2014.09); *A61L 9/14* (2013.01); *A61L 2209/133* (2013.01); *A61L 2209/134* (2013.01)

(58) Field of Classification Search
None
See application file for complete search history.

(56) References Cited

U.S. PATENT DOCUMENTS

| | | | |
|---|---|---|---|
| 8,170,405 B2 | 5/2012 | Harris | |
| 10,058,128 B2 | 8/2018 | Cameron et al. | |
| 10,632,222 B2 * | 4/2020 | Kelsen | G06K 7/10297 |
| 11,235,233 B1 * | 2/2022 | Peterson | A63F 13/28 |
| 2005/0167860 A1 | 8/2005 | Brooks | |
| 2011/0268605 A1 * | 11/2011 | Haran | A61L 9/125 422/4 |
| 2017/0216474 A1 | 8/2017 | Kelsen | |

FOREIGN PATENT DOCUMENTS

AU  2021250934  11/2021

* cited by examiner

*Primary Examiner* — Stephen T. Reed
(74) *Attorney, Agent, or Firm* — Kenneth L. Tolar

(57) ABSTRACT

An aroma cartridge for a video gaming system includes a hollow casing having a plurality of external walls and an interior chamber. Within the interior chamber is a volatile liquid having a discrete fragrance corresponding to a particular game feature, such as a character or a select environmental condition. The casing includes an integral heater and is in fluid communication with a mixer and an aroma-dispensing unit positioned near a gamer. A predetermined command signal from a controller activates the heater to vaporize the aromatic compound for transfer to the aroma-dispensing unit.

14 Claims, 4 Drawing Sheets

AROMA CARTRIDGE FOR A GAMING SYSTEM

CROSS REFERENCE TO RELATED APPLICATIONS

None.

BACKGROUND OF THE INVENTION

The present invention relates to a uniquely designed aroma cartridge for a gaming system that efficiently provides discrete aromas relating to a character or environmental conditions to an aroma-generating video game.

DESCRIPTION OF THE PRIOR ART

Video games and associated hardware peripherals are constantly evolving to enhance user experience and to further immerse the user in the virtual game environment. For example, some video games are adapted to operate with multiple video monitors so the gamer can view the game on a full screen while chatting or performing other tasks on another monitor. Larger or high-definition screens and complex software can create a more interactive, realistic experience that immerses the player in the virtual environment.

Despite continuous improvements to existing gaming technology, a player only uses three senses, i.e., eyesight, hearing, and cognition. Challenging only these three senses eventually becomes mundane, boring, and marginally stimulating. Accordingly, stimulating other senses can significantly enhance player experience.

The prior art includes at least one gaming system that releases aromas corresponding to gaming activity. For example, U.S. Pat. No. 11,235,233 to Peterson discloses a gaming system that generates aromas and other effects to enhance user experience. However, the device relies solely upon an electrical signal, piezoelectric crystals, and inherent aroma volatility to convert liquid fragrances to a gas for dispersal by a delivery system. Therefore, aroma generation and transmission may be limited in certain environmental conditions, and player experience may be significantly diminished.

Accordingly, there is currently a need in the art for an improved aroma delivery system that more efficiently transfers a liquid fragrance to a game player. The present invention satisfies that need by providing an aroma cartridge for a video game system having an integral heater for efficiently and effectively generating and dispensing vaporized aromas.

SUMMARY OF THE INVENTION

The present invention relates to an aroma cartridge for a video gaming system comprising a hollow casing having a plurality of external walls and an interior chamber. Within the interior chamber is a volatile liquid having a discrete fragrance corresponding to a particular game feature, such as a character or a select environmental condition. The casing includes an integral heater and is in fluid communication with a mixer and an aroma-dispensing unit positioned near a gamer. A predetermined command signal from a controller activates the heater to vaporize the volatile liquid for transfer to the aroma-dispensing unit.

It is therefore an object of the present invention to provide an aroma cartridge for a video gaming system that generates unique special effects to significantly enhance a user's experience.

It is therefore another object of the present invention to provide a cartridge for a video gaming system that emits various aromas congruent with a character, an environmental condition, or another aspect of a video game to provide a more interactive, immersive experience.

It is yet another object of the present invention to provide an aroma cartridge for a video gaming system having an integral heater to more efficiently vaporize fragrant liquids to enhance delivery to a gamer.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 1:
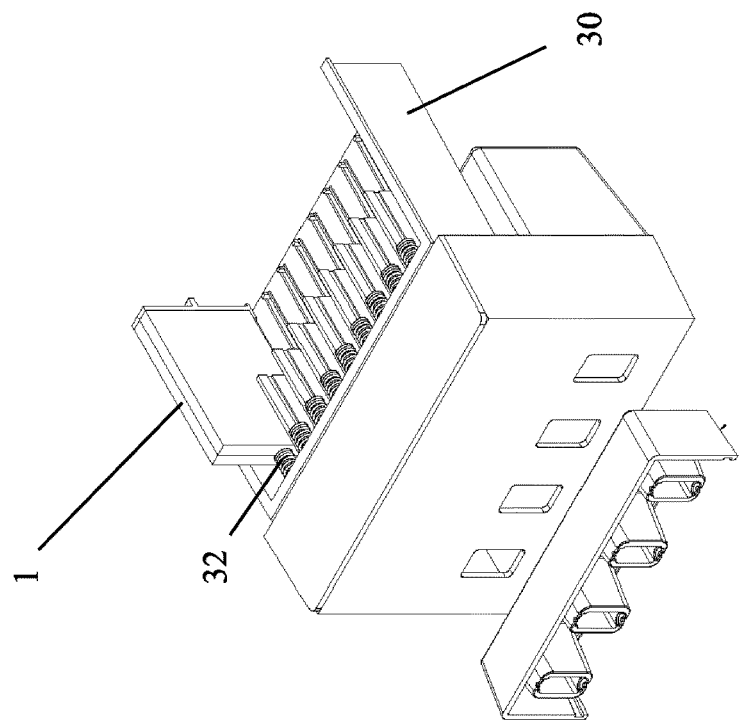
FIG. 1 is an isolated, perspective view of an exemplary cartridge holder and aroma delivery system for use with the cartridge disclosed herein.

The present invention relates to an aroma cartridge 1 for an aroma-generating video gaming system, such as the type described in U.S. Pat. No. 11,235,233, the specification of which is incorporated herein by reference. For example, the aroma gaming system may include a control unit 104 and a plurality of aroma dispensing units 106 positioned near a gamer. A typical video game is played using an electronic device with resident software, such as a computer, a laptop, a smart phone, a gaming-system controller, or any similar device having a computer processor. The gaming system further includes a mixing chamber 77 where a vaporized liquid from a cartridge is delivered. The mixing chamber 77 includes a plurality of inlet nozzles 80 in fluid communication with the dispensing units 106 for directing scented air to a gamer.

Each dispensing unit 106 includes a blower 108 with aroma delivery distributors (not pictured) positioned adjacent the intake side. The dispensing units can be oriented, adjusted, and independently controlled to create desired special effects. The gaming system also includes at least one cartridge holder 30 as depicted in FIG. 1 including one or more cartridge chambers 31 with biasing springs 32 and a snap receptacle for locking the cartridge 1 within a designated chamber.

The cartridge 1 as disclosed herein is designed for use with the type of gaming system as described above and includes a hollow casing 2 having a pair of opposing sidewalls 3, a front wall 4, a rear wall 10, a bottom wall 5, a top wall 6, and an interior fluid reservoir. Stored within the fluid reservoir is a volatile liquid 16 having a discrete fragrance corresponding to a particular game feature, such as a character or a select environmental condition. The rear wall 10 includes an outwardly projecting tab 11 that a user grasps when installing the cartridge within a cartridge chamber 31 or removing it therefrom.

A connector 25 on the bottom wall seats within the snap receptacle to lock the cartridge within its corresponding chamber against the bias of spring 32. The connector 25 is flanked by a pair of projections 26 that protect the connector 25 from impact damage if the cartridge is dropped or struck. Each sidewall includes an alignment pin 20 that guides the connector into the mating chamber.

Now referring to FIGS. 1-5, a first embodiment includes a heating element 53 positioned within the liquid reservoir having a contact 54 that is electrically connected to the game controller 104 when the cartridge is properly installed within the cartridge chamber. On the front wall of the housing, adjacent the heating element 53, is a dispensing nozzle 31 that is in fluid communication with inlet nozzles 80 on the gaming mixing chamber when the cartridge is installed within the cartridge holder. The heating element 53 may be perforated to facilitate passage of generated aroma to the dispensing nozzle 31. A command signal from the gaming system controller 104 activates the heater 53 to vaporize the volatile liquid which exits the dispensing nozzle 31 and is delivered to the mixing chamber 77.

Each heating element 53 has a discrete resistance rating so the gaming controller 104 can identify the type of aroma associated with a given heater. For example, a campfire aroma cartridge could have a heater rated at 1-10 ohms, a sea-air aroma cartridge could have a heater rated at 11-20 ohms, while a leather aroma cartridge heater could have a rating of 21-30 ohms. Therefore, when game conditions warrant the emission of a given fragrance, the controller can readily identify which heater to activate.

Figure 6:
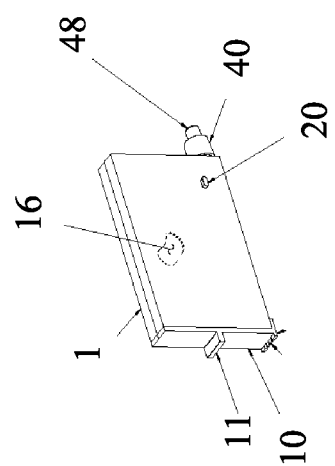
FIG. 6 is a perspective view of a second embodiment of the cartridge.
Figure 7:
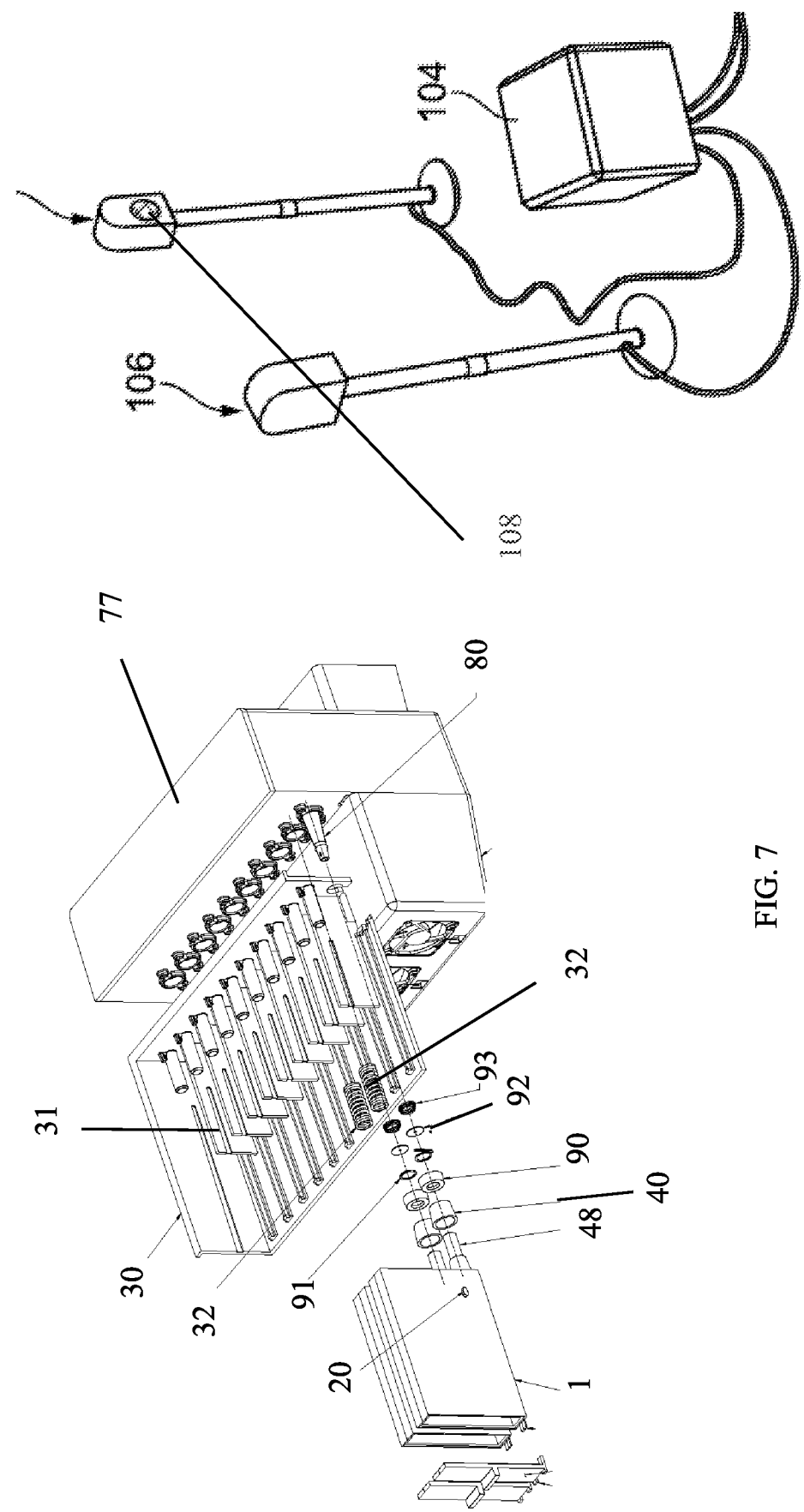
FIG. 7 is an exploded view of the embodiment of FIG. 6 and a corresponding cartridge holder.

Now referring to FIGS. 6 and 7, a second embodiment includes all the above-described external features for guiding and securing the cartridge within a mating cartridge chamber. In addition, the cartridge includes an absorbent tubular insert 48 positioned along the bottom of the reservoir and which exits the front wall of the cartridge. A cap 40 is attached to the protruding end of the insert to prevent it from dislodging from the cartridge. The cap may have a tapered internal passageway or similar structure that destroys the insert or otherwise prevents its reinsertion if removed.

A heater housing 90 is connected to the insert cap and includes a connector 91, a heating element 92 and a spring 93 that biases the heating element toward the insert. The insert 48 wicks the liquid to the heating element 92 which vaporizes it for delivery to the mixer inlet nozzles 80 and ultimately to the blowers 106. In lieu of the resistance ratings described above, each cartridge could have an indexing mechanism at a predetermined, discrete angle that only mates with a designated component in the corresponding cartridge chamber to allow the controller to identify each chamber by type of aroma and to activate its cartridge heater accordingly.

Figure 8:
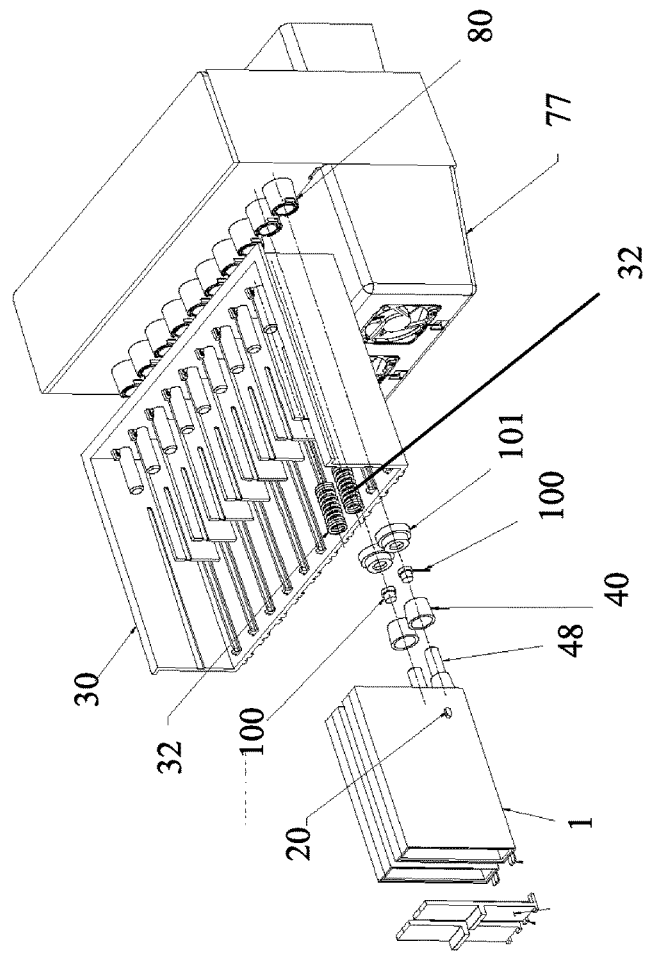
FIG. 8 is an exploded view of a third embodiment of the cartridge.
Figure 2:
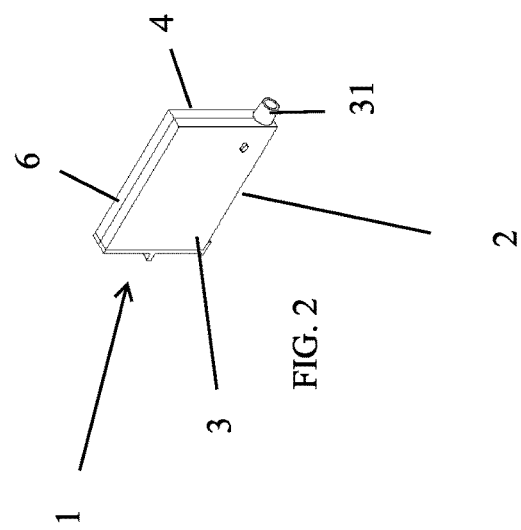
FIG. 2 is a perspective view of the cartridge according to a first embodiment.
Figure 4:
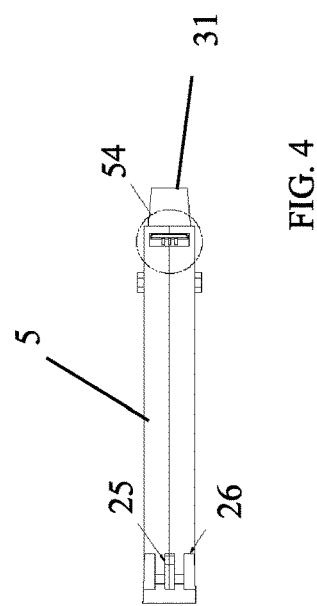
FIG. 4 is a bottom view of the cartridge of FIGS. 2 and 3.
Figure 5:
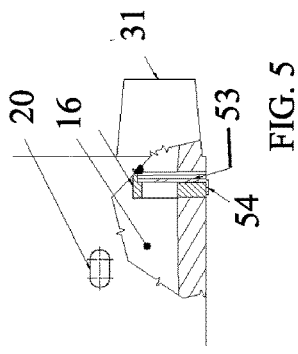
FIG. 5 is a cutaway view of the cartridge of FIGS. 1-4 depicting the internal heating element.
Figure 3:
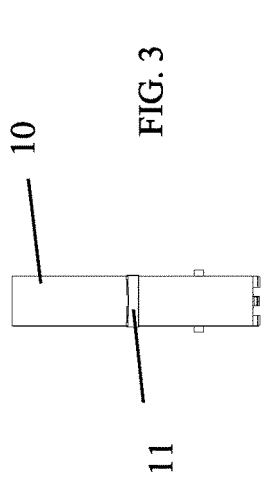
FIG. 3 is a rear view of the cartridge of FIG. 2.

Now referring to FIG. 8, a third embodiment of the cartridge is substantially similar to the cartridge described above and further includes a vibrating unit 100 in lieu of a heater that is encased within a housing 101. The housing 101 is attached to the insert cap such that the vibrating unit 100 engages the distal end of the tubular insert. Upon receipt of a predetermined command signal, the vibrator is activated to atomize the liquid into microscopic particles that are transmitted to the mixing chamber and nozzles and ultimately to a gamer. The mixing chamber will have sufficient air circulation to entrain the microscopic particles for delivery to the blowers.

The character and environmental fragrances are unlimited and could be created to identify certain characters and features of a given game. For example, for characters in the game "Overwatch," the aromas associated with each character could be as follows:

| Character ™ | Suggested Aroma with that Character |
|---|---|
| Ana | Elderly person, Medicine → Mothballs & Alcohol |
| Ashe | fire smell, gunshot, dynamite |
| Baptiste | To be determined |
| Bastion | Hydraulic fluid, gun powder, birds, machine oil |
| Brigette | To be determined |
| D.Va | Aircraft, hydraulics, perfume |
| Doomfist | To be determined |
| Genji | Leather, steel |
| Hanzo | Leather |
| Junkrat | Explosives, B.O., Bad breath, rubber |
| Lucio | Cheerios, healing |
| McCree | Whiskey, old leather, exploding gunpowder |
| Mei | Cold, blizzard, rain |
| Mercy | To be determined |
| Moira | New nail, perfume, healing |
| Orisa | Machine, glass or plastic |
| Pharah | Perfume, exploded gunpowder, rockets |
| Reaper | Shotguns firing, death, leather |
| Reinhart | Candy, glass or plastic |
| Roadhog | Bad B.O. fish, exploded gunpowder |
| Soldier: 76 | Rocket explosion, healing, gun powder |
| Sombra | Perfume, computer heat |
| Symmetra | perfume |
| Torbjorn | Machine gun firing, armor, sulfur |
| Tracer | Perfume, pine cones |
| Widowmaker | Death, perfume, exploded gunpowder |
| Winston | Gorilla, bananas, peanut butter, bad breath, glass or plastic |
| Wrecking Ball | Mechanical, muskrat, exploding gunpowder |
| Zarya | Perfume, working out B.O. |
| Zenyetta | Chestnuts, healing |

As another example, for the game "World of Warcraft," the environmental aromas could be:
Delicatessen, Restaurant, pub
Barbeque restaurant, beer
Campfire
Winter, cold
Ocean, salty air, fish smells, Swamp odors
Forge, Steel, rod, fire, smoke
Forest, trees, grass, flowers, herbs
Fresh farm soil, manure, hay
Various other aromas too numerous to mention The above-described device is not limited to the exact details of construction and enumeration of parts provided herein. Furthermore, the size, shape, and materials of construction of the various components can be varied without departing from the spirit of the present invention.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. An aroma-generating gaming system having a controller, a cartridge holder and at least one dispensing unit, an aroma cartridge comprising:
   a hollow casing having an outer shell and an interior fluid reservoir;
   a volatile liquid received within said fluid reservoir, said volatile liquid having a discrete fragrance corresponding to a particular game feature;

means for fixing said casing within said cartridge holder;

a dispensing nozzle on said outer shell and in fluid communication with said fluid reservoir and said dispensing unit; and an atomizer in fluid communication with said fluid reservoir and said dispensing nozzle for vaporizing said liquid to facilitate delivery to said dispensing unit.

2. The aroma cartridge according to claim 1 wherein said atomizer is a heating element.

3. The aroma cartridge according to claim 2 wherein said heating element is positioned within said reservoir.

4. The aroma cartridge according to claim 2 wherein said heating element is activated by said controller.

5. The aroma cartridge according to claim 3 wherein said heating element is perforated to facilitate passage of vaporized liquid to said dispensing nozzle.

6. The aroma cartridge according to claim 2 wherein said heating element has a discrete resistance rating to allow said controller to recognize a fragrance of said volatile liquid.

7. The aroma cartridge according to claim 2 further comprising an absorbent tubular insert received within said reservoir, said absorbent tubular insert having a distal end exiting said casing.

8. The aroma cartridge according to claim 7 further comprising a cap attached to the distal end of said absorbent tubular insert to prevent said absorbent tubular insert from dislodging from said casing.

9. The aroma cartridge according to claim 7 wherein said heating element engages said tubular insert.

10. The aroma cartridge according to claim 1 wherein said casing has an indexing mechanism at a predetermined, discrete angle for mating with a designated component in said cartridge holder to allow the controller to identify an aroma of the liquid within said reservoir.

11. The aroma cartridge according to claim 1 wherein said atomizer is a vibrating unit.

12. The aroma cartridge according to claim 1 further comprising a tab projecting from said casing that a user grasps when installing the cartridge within said cartridge holder.

13. The aroma cartridge according to claim 1 further comprising:

a connector on the outer shell of said casing for mating within a snap receptacle in said cartridge holder;

a pair of projections flanking said snap connector for protecting said connector from impact damage.

14. The aroma cartridge according to claim 13 further comprising at least one alignment pin on the outer shell of said casing for guiding said connector into said cartridge holder.

* * * * *